(12) United States Patent
Titterton et al.

(10) Patent No.: US 7,594,428 B2
(45) Date of Patent: *Sep. 29, 2009

(54) APPARATUS AND METHOD FOR ELIMINATING THE BREAKTHROUGH PEAK IN DIFFERENTIAL DETECTORS

(75) Inventors: Alan Titterton, Yarm (GB); Max A. Haney, Houston, TX (US)

(73) Assignee: Viscotek Corporation, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/072,149

(22) Filed: Feb. 25, 2008

(65) Prior Publication Data

US 2008/0245133 A1      Oct. 9, 2008

Related U.S. Application Data

(63) Continuation-in-part of application No. 11/249,839, filed on Oct. 12, 2005, now Pat. No. 7,334,457.

(51) Int. Cl.
*G01N 11/04* (2006.01)

(52) U.S. Cl. ..................................... 73/54.04; 73/54.06

(58) Field of Classification Search ................. 73/54.04, 73/54.06
See application file for complete search history.

(56) References Cited

U.S. PATENT DOCUMENTS

| | | | | |
|---|---|---|---|---|
| 4,627,271 A | * | 12/1986 | Abbott et al. | 73/54.06 |
| 6,708,553 B2 | * | 3/2004 | Bures | 73/54.04 |
| 6,712,085 B2 | * | 3/2004 | Weissgerber et al. | 137/12 |
| 6,877,361 B2 | * | 4/2005 | Bures | 73/54.04 |
| 2002/0134262 A1 | * | 9/2002 | Kaser et al. | 101/219 |
| 2002/0166367 A1 | * | 11/2002 | Bures | 73/54.04 |

* cited by examiner

*Primary Examiner*—Andre J Allen
(74) *Attorney, Agent, or Firm*—Matthews, Lawson & Bowick PLLC

(57) ABSTRACT

The method comprising the steps of engaging the flow circuit of the detector with a reference fluid, accepting a sample in the flow circuit of the detector, sensing an attribute of the sample for determining a characteristic of the sample, changing the direction of the flow of the sample in the flow circuit, and purging the sample from the flow circuit such that the flow circuit is ready to accept another sample. Another method provides the steps of engaging the flow circuit of the detector with a reference fluid, inserting a sample in the flow circuit juxtaposed to the reference fluid, sensing an attribute of the sample for determining a characteristic of the sample, and deviating the direction of the flow of the sample from the flow circuit for purging the sample from the flow circuit such that the reference fluid is maintained in the flow circuit.

The apparatus comprises a detector for analyzing a sample comprising a reference cell and a sample cell such that the detector is charged with a reference fluid, a switching valve in communication with the sample cell of the detector, and one or more delay volumes and the reference cell in communication with the switching valve. The sample is juxtaposed the reference fluid for engaging the sample cell for analysis, the analyzed sample engages the switching valve for alternately diverting the analyzed sample from the flow circuit and for maintaining the detector charged with the reference fluid.

31 Claims, 14 Drawing Sheets

APPARATUS AND METHOD FOR ELIMINATING THE BREAKTHROUGH PEAK IN DIFFERENTIAL DETECTORS

CROSS REFERENCE TO RELATED APPLICATION

The present application is a continuation-in-part application of the application of Alan Titterton, U.S. Ser. No. 11/249,839, filed Oct. 12, 2005, entitled IMPROVED MULTI-CAPILLARY VISCOMETER APPARATUS AND METHOD, now U.S. Pat. No. 7,334,457 issued Feb. 26, 2008.

FIELD OF THE INVENTION

The present invention relates to differential detectors, comparative sensors or any device that involves an analysis between two or more samples or specimen. More particularly, the present invention relates to eliminating the breakthrough peak associated with differential detectors, comparative sensors or any device that involves an analysis between two or more samples or specimen.

BACKGROUND OF THE INVENTION

Differential detectors, comparative sensors or any other device that involves an analysis between two or more samples or specimen may result in a breakthrough peak that distracts from the measurement. A multitude of detectors or sensors are susceptible to the same or similar problems. By way of example, and without limitation, viscometers, refractive index detectors, deflection detectors, reflective detectors and any combination of refractive index, ultra-violet, fluorescent, radiochemical, electrochemical, near-infra red, mass spectroscopy, nuclear magnetic resonance, and light scattering are potential instruments, detectors and sensors applicable to the present invention.

The refractive index of a material is the most important property of any optical system that uses refraction. The refractive index is used to calculate the focusing power of lenses, and the dispersive power of prisms, and to measure the concentrations as well as elemental analyses. Since the refractive index is a fundamental physical property of a substance, it is often used to identify a particular substance, confirm its purity, or measure its concentration. The refractive index is used to measure solids, liquids, and gases. Most commonly it is used to measure the concentration of a solute in an aqueous solution. A refractometer is the instrument used to measure refractive index.

The refractive index or index of refraction of a medium is a measure for how much the speed of light, or other waves such as sound waves, is reduced inside the medium. For example, typical glass has a refractive index of 1.5, which means that light travels at 1/1.5=0.67 times the speed in air or vacuum. Two common properties of glass and other transparent materials are directly related to their refractive index. First, light rays change direction when they cross the interface from air to the material, an effect that is used in lenses and glasses. Second, light reflects partially from surfaces that have a refractive index different from that of their surroundings.

The refractive index, n, of a medium is defined as the ratio of the phase velocity c of a wave phenomenon such as light or sound in a reference medium to the phase velocity $v_p$ in the medium itself:

$$n = \frac{c}{v_p}$$

The refractive index, n, is most commonly used in the context of light with a vacuum as a reference medium, although historically other reference media, e.g., air at a standardized pressure and temperature, have been common. It is usually given the symbol n. In the case of light, refractive index, n, equals:

$$n = \sqrt{\epsilon_r \mu_r},$$

where $\epsilon_r$ is the material's relative permittivity, and $\mu_r$ is the material's relative permeability. For most materials, $\mu_r$ is very close to 1 at optical frequencies, therefore, n is approximately $\sqrt{\epsilon_r}$.

The refractive index, RI, detector is the only universal detector in high-performance liquid chromatography (HPLC). HPLC is a form of column chromatography used frequently in biochemistry and analytical chemistry. It is also sometimes referred to as high-pressure liquid chromatography. HPLC is used to separate components of a mixture by using a variety of chemical interactions between the substance being analyzed (analyte) and the chromatography column.

The detection principle involves measuring of the change in refractive index of the column effluent passing through the flow-cell. The greater the RI difference between sample and mobile phase, the larger the imbalance will become. Thus, the sensitivity will be higher for the higher difference in RI between sample and mobile phase. On the other hand, in complex mixtures, sample components may cover a wide range of refractive index values and some may closely match that of the mobile phase, becoming invisible to the detector. The RI detector is a pure differential instrument, and any changes in the eluent composition require the rebalancing of the detector. This factor severely limits RI detector application in the analyses requiring the gradient elution, where the mobile phase composition is changed during the analysis to effect the separation. Two basic types of RI detectors are on the market today. Both require the use of a two-path cell where the sample-containing side is constantly compared with the non-sample-containing reference side.

The deflection detector is based on the deflection principle of refractometry. Refractometry provides that the deflection of a light beam is changed when the composition in a sample flow-cell changes in relation to the reference side as eluting sample moves through the system. When no sample is present in the cell, the light passing through both sides is focused on a photodetector, usually photoresistor. As sample elutes through one side, the changing angle of refraction moves the beam. This results in a change in the photon current falling on the detector that unbalances it. The extent of unbalance, which can be related to the sample concentration, is recorded on a recorder.

The advantages of this type of detector are: universal response; low sensitivity to dirt and air bubbles in the cells; and the ability to cover the entire refractive index range from 1.000 to 1.750 RI with a single, easily balanced cell. The disadvantages are: a general disability to easily remove and clean or replace the cell when filming or clogging occurs, the need to flush the sample-side intermittently, static solvent causing baseline drift and the need to refresh, replenish or recharge the reference-side.

Another relevant detector is a reflective detector. The reflective detector is a refractive index detector based on the Fresnel principle. In the reflective detector, the light beam is reflected from the liquid-glass interface in the detecting photocell. The introduction of sample into one cell causes light to be refracted at a different angle. The deflection of the light beam from the photoresistor causes the appearance of the electrical signal. Here, too, this difference between sample-cell signal and reference-cell signal is output to a recorder or data handling system as a peak.

The major advantage of the reflective detector is a very high sensitivity since the optics allow a higher concentration of signal in a particular RI range than is possible in other wide-range detectors. Other advantages include the ability to operate at extremely low flow rates with very low-volume cells, easy cell accessibility, and low cost. The disadvantages of the reflective detector are the incredible sensitivity to the flow and pressure fluctuations, and the need for changing prisms to accommodate either high or low RI solvents and the need to manually adjust the optical path when making solvent changes.

The refractive index of an analyte is a function of its concentration. Change in concentration is reflected as a change in the RI. A refractive index detector for liquid chromatography should be sensitive to changes as small as $10^{-7}$ RI units corresponding to a concentration change of 1 ppm. Presence of dissolved air, changes in solvent composition, improper mixing and column bleed will contribute to baseline drift. Eluent pressure change of 15 psi will cause the change of $1\times10^{-6}$ RI unit and $1°$ C. temperature variation will be equivalent to the change of $600\times10^{-6}$ RI units. Thus it is obvious that both of these parameters must be closely controlled, especially temperature. To operate at high sensitivities, a RI detector must usually be thermostated ($\pm0.01°$ C.), actually the using of the water bath connected to the detector head does not give required temperature stability, alternately, passive thermostabilisation with massive metallic block usually gives much better results.

All the above-noted apparatus, including differential detectors, comparative sensors or any device that involves an analysis between two or more samples or specimen, suffer from having a breakthrough peak that delays processing and contaminates flow paths and capillaries. Therefore, of primary concern in the present invention is the removal of the breakthrough peak, and thus, the processing delays and the contamination of the flow paths and capillaries.

It is, therefore, a feature of the present invention to remove the associated breakthrough peak.

A feature of the present invention is to improve processing efficiency by reducing processing delays.

Another feature of the present invention is to inherently prevent the contamination of the flow paths and the capillaries.

Another feature of the present invention is to reduce baseline drift by providing consistent solvent composition.

Another feature of the present invention is to reduce baseline drift by removing dissolved air from the measurement cells.

Yet another feature of the invention is to reduce baseline drift by improper mixing.

Still another feature of the present invention is to reduce baseline drift by preventing the effect of column bleed.

Another feature of the present invention is to reduce the sensitivity to the flow fluctuations.

Yet another feature of the present invention is to reduce the sensitivity to the pressure fluctuations.

Still another feature of the present invention is to easily clean the reference cell when filming or clogging occurs.

Additional features and advantages of the invention will be set forth in part in the description which follows, and in part will become apparent from the description, or may be learned by practice of the invention. The features and advantages of the invention may be realized by means of the combinations and steps particularly pointed out in the appended claims.

SUMMARY OF THE INVENTION

To achieve the foregoing objects, features, and advantages and in accordance with the purpose of the invention as embodied and broadly described herein a method for purging samples from a flow circuit of a detector for analyzing samples is provided. The method comprising the steps of engaging the flow circuit of the detector with a reference fluid, accepting a sample in the flow circuit of the detector, sensing an attribute of the sample for determining a characteristic of the sample, changing the direction of the flow of the sample in the flow circuit, and purging the sample from the flow circuit such that the flow circuit is ready to accept another sample.

Another method provides the steps of engaging the flow circuit of the detector with a reference fluid, inserting a sample in the flow circuit juxtaposed to the reference fluid, sensing an attribute of the sample for determining a characteristic of the sample, and deviating the direction of the flow of the sample from the flow circuit for purging the sample from the flow circuit such that the reference fluid is maintained in the flow circuit.

The apparatus comprises a detector for analyzing a sample comprising a reference cell and a sample cell such that the detector is charged with a reference fluid, a switching valve in communication with the sample cell of the detector, and one or more delay volumes and the reference cell in communication with the switching valve. The sample is juxtaposed the reference fluid for engaging the sample cell for analysis, the analyzed sample engages the switching valve for alternately diverting the analyzed sample from the flow circuit and for maintaining the detector charged with the reference fluid.

DETAILED DESCRIPTION OF THE EMBODIMENTS

For a further understanding of the nature, function, and objects of the present invention, reference is made to the following detailed description taken in conjunction with the accompanying drawings. Detailed descriptions of embodiments of the apparatus are provided herein, as well as modes of carrying out and employing the embodiments of the present invention. It is to be understood, however, that the present apparatus may be embodied in various forms. The description provided herein relates to the common components of sample capillary, delay volume components, reference capillary and diverter valve which may form only part of a more complex circuit. Therefore, specific details disclosed herein are not to be interpreted as limiting, but rather as a basis for the claims and as a representative basis for teaching one skilled in the art to employ the present embodiments of one form of the apparatus or method in virtually any appropriately detailed system, structure or manner. The embodiments described herein are considered illustrative of both the processes taught by the described embodiments of products and articles of manufacture yielded in accordance with the present embodiments of one form of the apparatus. The inventive device and method can be used in a multi-capillary viscometer for which the basic operating principles are disclosed in U.S. Pat. No. 4,463,598 to Haney, in U.S. Pat. Nos. 4,627,271 and 4,578,990 to Abbott, et al., and in U.S. Pat. No. 5,637,790 to de Corral.

In the prior art, multi-capillary viscometers are constructed and operated such that a reference flow of solvent may be maintained during a measurement by inserting a delay volume component in front of a reference capillary. The delay volume component initially contains pure solvent at the beginning of the analysis. It provides a continuing flow of solvent to a reference capillary while sample flows though a sample capillary. A limitation of such prior art multi-capillary viscometers, whether used only for viscosity measurements or in combination with other detectors in GPC or SEC analysis, is typically referred to as a breakthrough peak. The breakthrough peak is an unwanted instrument response resulting from the discharge of sample fluid from the delay volume component through a reference capillary after pressures have been detected or sensed that are useful in determining information about the viscosity of the sample. The breakthrough peak can last for a substantial period of time after the measurement process is completed because the delay volume spreads the peak, thereby delaying the measurement of the next sample.

Figure 1:
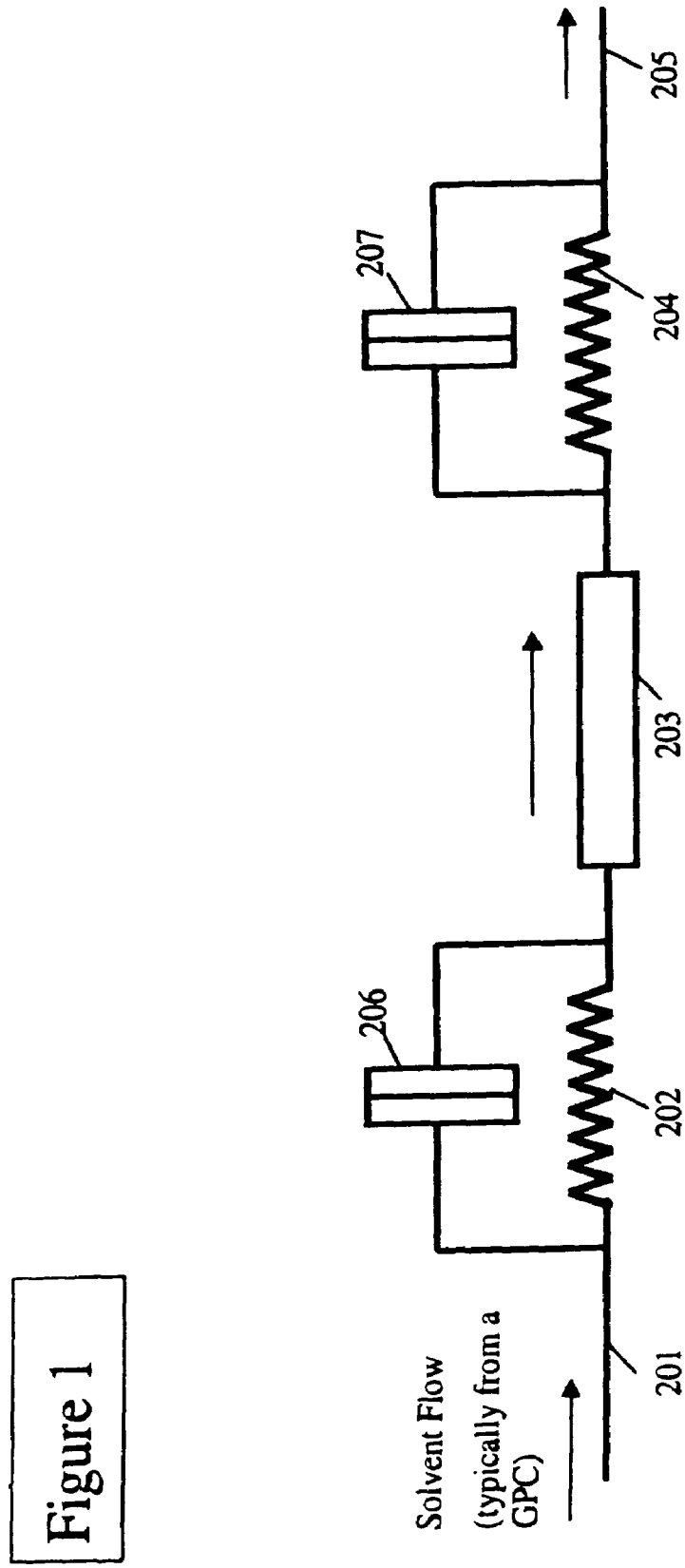
FIG. 1 illustrates a schematic view of a general multi-capillary viscometer.

The cause of the breakthrough peak effect can be appreciated by reference to FIG. 1 accompanied with the following description. FIG. 1 illustrates schematically a simple multi-capillary viscometer and can be described as an operating circuit. The operating circuit consists of an inlet tube 201 coupled in series to a narrower bore capillary tube 202 referred to as the sample capillary, a delay volume component 203 which has a hold-up volume of significantly large capacity, a second narrow bore capillary tube 204 referred to as the reference capillary, and finally an exit tube 205. When a fluid such as a solvent is pumped through the circuit, a differential pressure will be generated, mainly across the capillary tubes since they have a narrower cross-sectional area than the connecting tubing and other components in the circuit. The pressure across each capillary may be monitored continuously by means of suitable transducers 206, 207. A sample solution is injected into the flowing solvent stream and is carried through the circuit. Its passage through the sample capillary 202 will typically cause an increased pressure drop because of the viscosity of the sample. The increased pressure drop will be detected by the transducer 206 across the respective sample capillary 202. However, the pressure monitored by the transducer 207 across the reference capillary 204 will remain substantially unaltered since it will still be receiving solvent eluting from the delay volume component 203. The relative viscosity may be mathematically derived using the ratio of the pressure drop across the sample capillary 202 to the pressure drop across the reference capillary 204 as described in, for example, U.S. Pat. Nos. 4,627,271 and 4,578,990, Abbott, et al. The relative viscosity will increase as sample flows into the viscometer.

The volume of the delay volume component 203 is selected to be sufficient to supply the reference capillary 204 with solvent during the measurement process. Eventually, all the sample solution will emerge from the sample capillary 202 and enter the delay volume component 203. The pressure across the sample capillary 202 will return to the baseline value and the useful part of the measurement cycle is over. However, the sample will eventually progress all the way through the delay volume component 203 and enter the reference capillary 204 where it will cause an increase in pressure, measured by the transducer 207 associated with the reference capillary 204. This increase in pressure causes a decrease in the measured relative viscosity, which is the cause of the breakthrough peak.

Figure 2A:
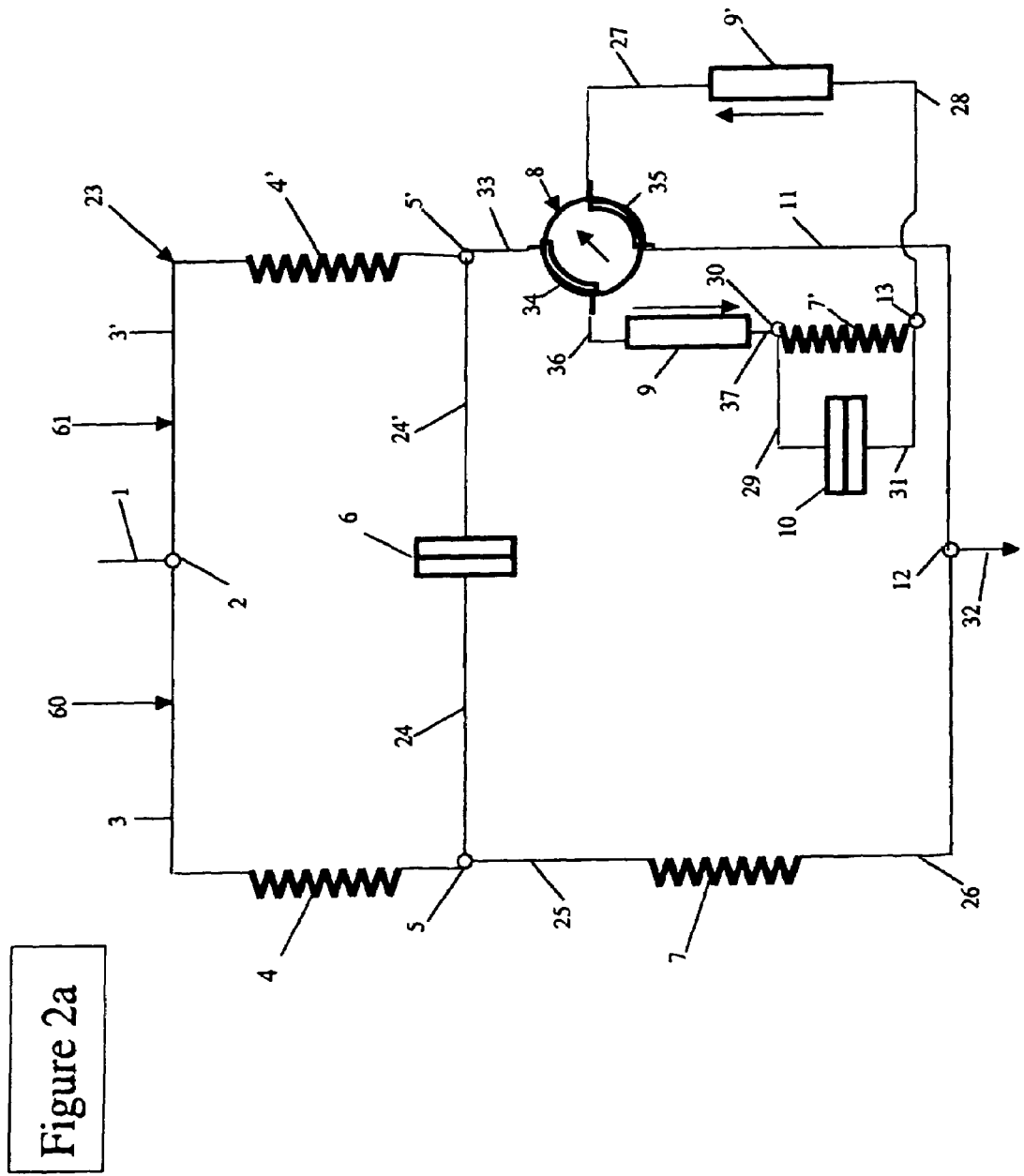
FIG. 2a illustrates a block diagram of one embodiment of the apparatus with two delay volume components and a fluid diverting component in orientation A.

FIG. 2a illustrates one embodiment of the present embodiments of one form of the apparatus comprising a fluid viscosity measurement circuit 23 having components connected together preferably using conventional tubing connectors, fittings or unions and connecting tubing. The fluid viscosity measurement circuit 23 preferably has a fluid insertion or injection tube 1 through which a fluid is inserted. Fluid viscosity measurement circuit 23 preferably has a first fluid flow circuit 60 and a second fluid flow circuit 61.

In the embodiment illustrated by FIG. 2a, the fluid insertion or injection tube 1 attaches to a split junction 2, which can include but is not limited to a T-bridge split junction. The split junction 2 is attached to two lengths of pipe or tubing 3, 3'. The two lengths of pipe or tubing 3, 3' are attached to the split junction 2 so as to allow a fluid to move through the split junction 2 into the length of pipe or tubing 3 and the other length of pipe or tubing 3'. The length of pipe or tubing 3 is connected between the split junction 2 and a first capillary 4 in the flow circuit 60. The first capillary 4 is preferably a conventional fluid capillary, which is preferably a tube, having a relatively small inside diameter (typically, but not limited to, the range of about 0.009" to 0.014") in comparison to the relatively large inside diameter of other fluid components in the circuit (typically, but not limited to 0.04" or more for connecting tubing and fittings and 0.062" or more for delay volumes). The first capillary 4 serves to provide a flow restriction within the fluid viscosity measurement circuit. The terms "capillaries" or "capillary" are used throughout this application in their normal and customary manner to include, for example, any structure with a cross-sectional hollow portion having a relatively small inside diameter to produce a pressure drop higher than that produced by other individual components of the fluid viscosity measurement circuit.

The length of pipe or tubing 3' is connected between the split junction 2 and a first capillary 4' of the second flow circuit 61. The capillaries 4, 4' are preferably conventional fluid capillaries. The first capillary 4 is preferably connected to a second split junction 5. The first capillary 4' is preferably connected to a second split junction 5'. The first split junction 5 and the second split junction 5' are preferably connected to a transducer tube or line 24, 24', respectively. The transducer tubes or lines 24, 24' are preferably connected to the second split junctions 5, 5', respectively, and to a transducer 6. The terms "transducer" or "transducers" are used throughout this application in their normal and customary manner to include, for example, any structure or apparatus operable for sensing or measuring fluid differential pressures and, more particularly, differential pressure transducers of the type described in the Abbot, et al. and De Coral patents wherein two cavities are separated by a diaphragm which is deflected by a pressure difference in the cavities to produce an electrical signal proportional to the pressure differential.

The transducer 6, and all transducers referred to herein, is preferably connected in a "dead-end" manner, such that only the inlet ports of the transducers remain open after the transducer lines and cavities are filled and purged for operation, and pressure is transmitted by static fluid in the transducer lines and cavities to the transducer diaphragm. The transducer 6 and all transducers referred to herein may also be connected in a "flow-through" manner, wherein inlet, outlet or purge ports of each cavity of the transducer are connected such that fluid flowing through one or more of the other components in the circuit also flows through the transducer cavities, and fluid pressure is transmitted to the transducer diaphragm by the fluid flowing through the transducer cavity.

The split junction 5 preferably connects to a fluid tube 25. The fluid tube 25 preferably connects to a capillary 7. The capillary 7 preferably connects to another fluid tube 26. The fluid tube 26 preferably connects to a split junction 12. The split junction 12 preferably connects to yet another fluid tube 32.

The split junction 5' in the second fluid flow circuit 61 preferably connects to a fluid tube 33. The fluid tube 33 preferably connects to a fluid path diverter valve 8. The fluid path diverter valve 8 preferably contains a plurality of fluid pathways 34, 35. The terms "diverter valve" or "valve" are used in this application in their normal and customary manner, and by way of example, refers to any valve or structure operable to selectively direct or align the flow of fluid from one fluid pathway to another and may include, but is not limited to, a valve operable for that purpose in a prescribed or automated fashion, which may be, but is not limited to, electrical, pneumatic or timed operation or activation. The term "diverter valve" as used in this application can be, but is not limited to a 4-port, 2 position plug valve, such as Hamilton HV-86779. As shown in FIG. 2a, a first fluid pathway 34 is connected to a first fluid tube 36, and a second fluid pathway 35 is connected to a second fluid tube 27. The first fluid tube 36 is connected to a first delay volume 9. The first delay volume 9 is connected to a downstream fluid tube 37. The term "delay volume" is used in this application in its normal and customary manner, and for example, includes any means of delaying a fluid's arrival at another point in the fluid circuit, which may include, but is not limited to, increased volume tubing or reservoirs. A typical delay volume can include, but is not limited to a packed column. The downstream fluid tube 37 is preferably connected to a split junction 30. A capillary 7' is also connected to the split junction 30. The capillary 7' can be, but is not necessarily, substantially identical to the corresponding capillary 7. A transducer line or tube 29 is also attached to the split junction 30.

The transducer line or tube 29 is preferably connected to a transducer 10. The transducer 10 is preferably a conventional transducer utilized in measuring fluid viscosity. The transducer 10 is preferably connected in the "dead-end" manner described above for the center transducer 6. The transducer 10 and the center transducer 6 are preferably substantially identical. The transducer 10 is also connected to a transducer line or tube 31 such that the connections of transducer line or tube 29 and transducer line or tube 31 are on substantially opposite sides of the diaphragm associated with the transducer 10. The transducer line or tube 31 is connected to a split junction 13. The capillary 7' is likewise connected to the split junction 13. A fluid tube line 28 is preferably connected to the split junction 13 and to a second delay volume 9'. The first delay volume 9 and the second delay volume 9' are preferably substantially identical. The second delay volume 9' is preferably connected on its opposite end to a fluid tube 27. The fluid tube 27 is preferably connected to the second fluid pathway 35 of the fluid path diverter valve 8. The second fluid pathway 35 is also preferably connected on its opposite end to a fluid tube 11. The fluid tube 11 is connected to the split junction 12.

Figure 2B:
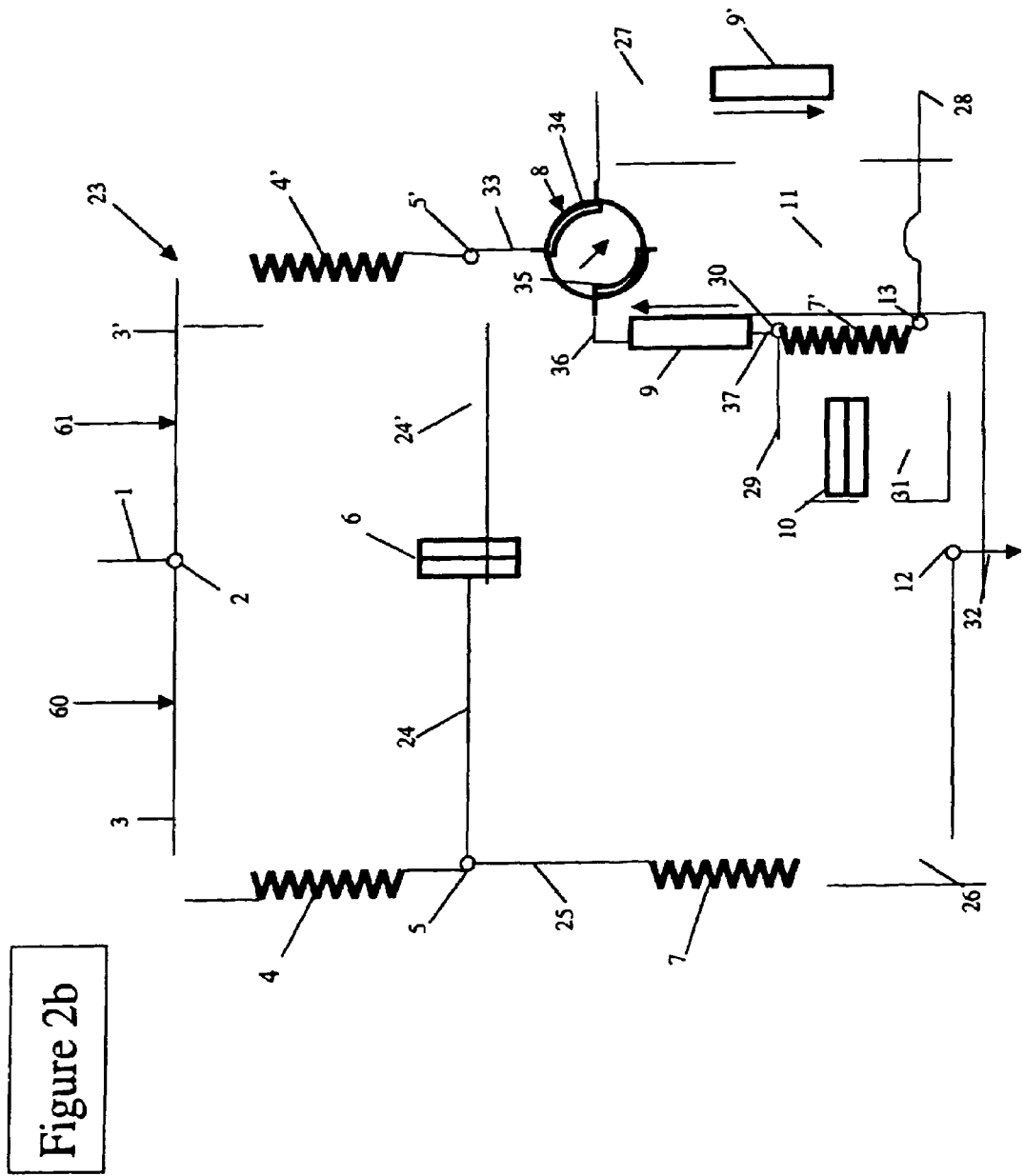
FIG. 2b illustrates a block diagram of one embodiment of the apparatus with two delay volume components and a fluid diverting component in orientation B.

FIG. 2b, illustrates another embodiment of an apparatus of the present invention similar to the embodiment illustrated in FIG. 2a. The embodiment illustrated in FIG. 2b is similar to the embodiment illustrated in FIG. 2a except in the embodiment in FIG. 2b, the fluid path diverter valve 8 is rotated to another position. Particularly, the fluid path diverter valve 8 is positioned such that the fluid pathway 34 is aligned between the respective fluid tubes 33, 27, and the fluid pathway 35 is aligned between the respective fluid tubes 11, 36.

As appreciated by one skilled in the art, the embodiment of the apparatus disclosed in FIG. 2a operates in, but is not limited to, substantially the following manner. When in pre-sample testing mode, a stream of reference fluid or solvent runs through the system and follows one of a plurality of pathways. As the solvent flows into the system through the injection tube 1, the solvent moves until it approaches the split junction 2, at which point the fluid stream of solvent is divided to flow into both fluid tubes 3, 3. The solvent then flows through the two first capillaries 4 and 4' and approaches the two split junctions 5, 5', respectively. The fluid pressure at the two split junctions 5, 5', respectively, is transmitted by the fluid in the transducer tubes or lines 24, 24' to opposite sides of the transducer 6. The fluid that flows into the fluid tube 25, adjacent to the second split junction 5, proceeds to flow through the capillary 7, through the fluid tube 26 and then to the split junction 12. Alternately, the fluid that flows from the fluid tube 33, adjacent to the second split junction 5', flows into the first fluid pathway 34. The fluid then flows into the fluid tube 36 and then into the delay volume 9. The fluid stream then flows into the fluid tube 37, which connects to the split junction 30, and then into the capillary 7'. The fluid pressure at the split junction 30 is transmitted by the fluid in the transducer line or tube 29 to one side of the transducer 10. The fluid entering the split junction 30 from the delay volume 9 flows through the capillary 7' to the split junction 13. The pressure of the fluid at the split junction 13 is transmitted by the fluid in transducer line or tube 31 to one side of the transducer 10, thus enabling the transducer 10 to produce a signal substantially corresponding to the differential pressure across the capillary 7' (the difference in fluid pressures upstream and downstream of the capillary 7'). The fluid flow, when it reaches the split junction 13, flows into the fluid tube 28, then into the delay volume 9' and then into the fluid tube 27. The fluid flows into the fluid pathway 35 of the fluid path diverter valve 8 and then into the fluid tube 11. The fluid then flows into the split junction 12. The fluids in the fluid tube 26 and the fluid tube 11 meet at the split junction 12, then exit via the fluid tube 32 which is connected to the split junction 12. Reference fluid may be flowed continuously through the measurement circuit to allow base line readings to be developed from the transducers 6, 10 with the measurement circuit full of flowing reference fluid.

With the fluid diverter valve 8 positioned as disclosed in FIG. 2b, the measurement circuit operates in a similar manner as described in FIG. 2a. The fluid flows from the tube 33, into the fluid pathway 34 and then into the fluid tube 27. The fluid then enters the delay volume 9' and flows into the fluid tube 28. The fluid then flows into the split junction 13 connecting the transducer line or tube 31 and the capillary 7'. The pressure of the fluid at the split junction 13 is transmitted by the fluid in the transducer line or tube 31 to one side of the transducer 10. The fluid that flows through the capillary 7' enters split junction 30 and then into the fluid tube 37. The pressure of the fluid at the split junction 30 is transmitted by the fluid in the transducer line or tube 29 to one side of the transducer 10. The fluid exiting the fluid tube 37 flows into the delay volume 9. The fluid then flows from the delay volume 9 into the fluid tube 36, which is connected to the fluid pathway 35. The fluid flows into the fluid pathway 35, which is connected to the fluid tube 11 and then to the split junction 12.

To measure the viscosity of a sample fluid with the viscosity measurement circuit of the present invention as illustrated in FIG. 2a, the sample is injected or added into the reference fluid at or upstream of the inlet to the measurement circuit at the injection tube 1. The sample then flows in solution with the reference fluid along the same fluid pathway as described above for FIG. 2a. The delay volume 9 delays the arrival of the sample solution at the capillary 7' such that the differential pressures across the corresponding capillaries 7, 7' may be sensed by the transducers 6, 10 when the capillary 7 contains sample material and the capillary 7' contains only the solvent or reference fluid. Hence, the pressure drop sensed by the sample transducer 6 will be different than the pressure drop sensed at that time by the reference transducer 10 because the reference transducer 10 will still be sensing a differential pressure associated with the pure solvent in the capillary 7'. This enables the transducers 7, 10 to produce signals substantially corresponding to the pressure drops across the capillary containing pure solvent and the capillary containing the sample solution for use in determining relative viscosity, which may be mathematically related to other characterizations of the sample's properties, such as intrinsic viscosity, inherent viscosity, specific viscosity and reduced viscosity, by methods known in the art, such as is described in, for example, the Abbott, et al. patent and the De Corral patent. The transducer signals may also be used in combination with the signals produced by a refractometer or similar concentration detector, which is part of a GPC system, to determine other information about the sample's properties such as, for example, molecular weight distribution.

After the relative differential pressure information is obtained, the fluid path diverter valve 8 may be switched to realign the valve, in a conventional fashion, such that the flow of fluid through the reference capillary 7' is reversed as illustrated in FIG. 2b to move the sample fluid in a direction from the capillary 7' toward the split junction 30 and the fluid path diverter valve 8, through the fluid path diverter valve 8, and then through the fluid tube 11 to the split junction 12. By switching the fluid path diverter valve 8 in this manner, another relative differential pressure measurement may be taken of a new test sample flowing as per the configuration illustrated in FIG. 2b. Reversing the direction of flow through the capillary 7' decreases or eliminates the unwanted breakthrough peak associated with the flow of the sample solution through that capillary, thus reducing the time needed for a successive analysis of another sample.

Figure 3A:
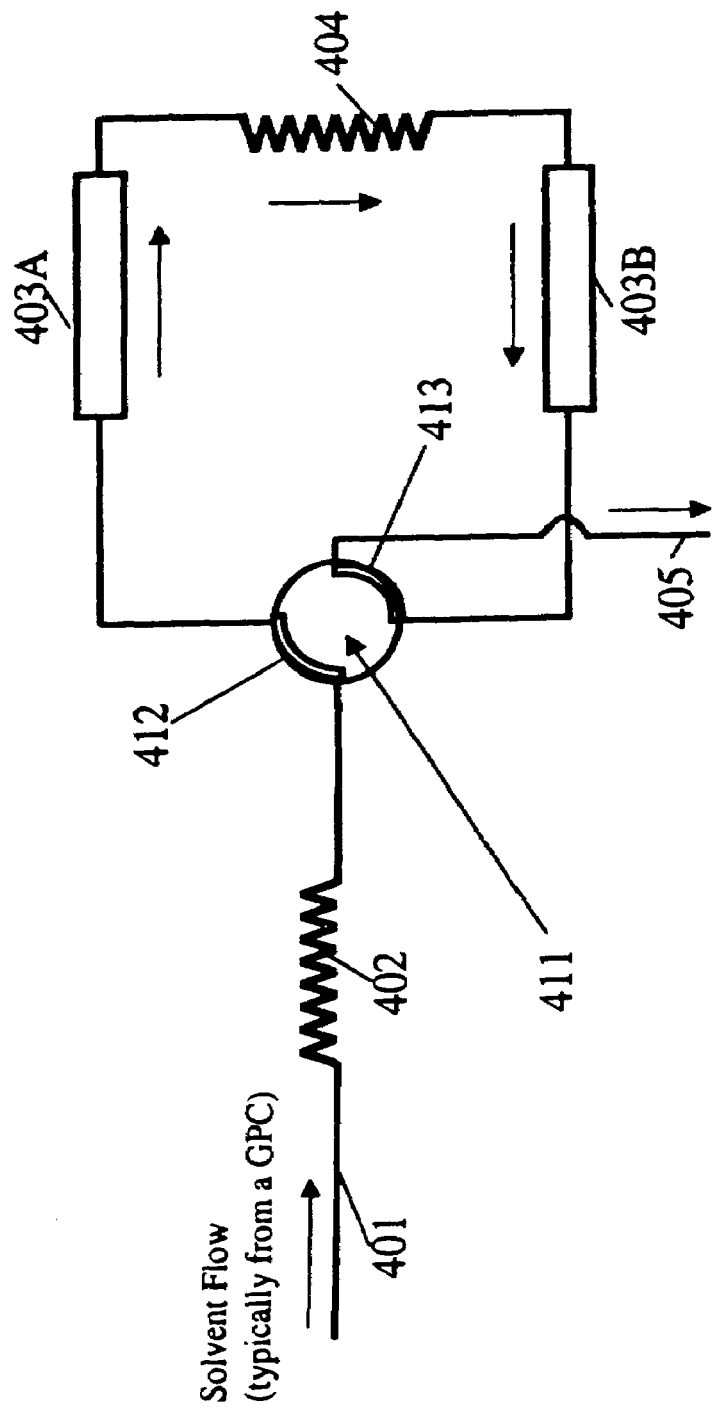
FIG. 3a is a block diagram of one embodiment of the subcircuit of the apparatus with two delay volume components and a fluid diverting component in orientation A.
Figure 3B:
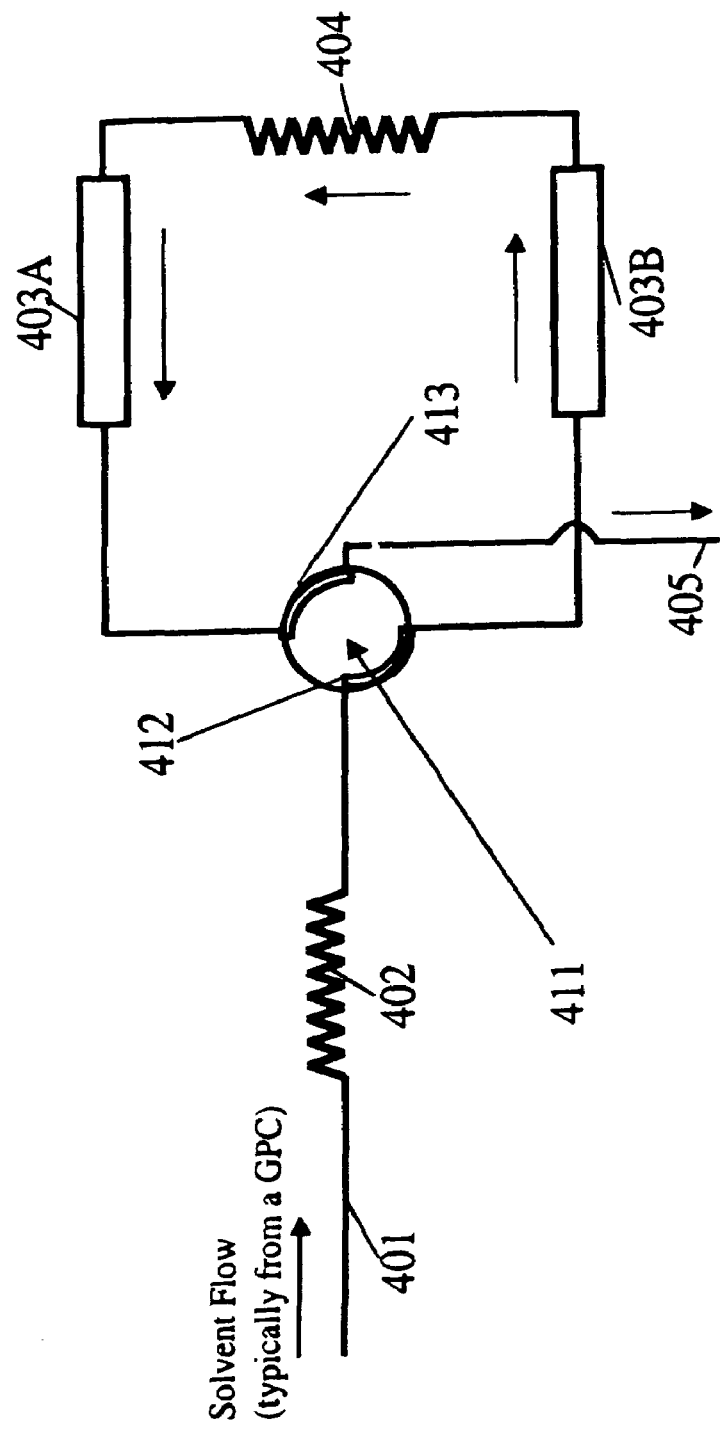
FIG. 3b is a block diagram of one embodiment of the subcircuit of the apparatus with two delay volume components and a fluid diverting component in orientation B.

FIGS. 3a and 3b represent one embodiment of a subcircuit of the apparatus of the present invention in alternative positions. A second delay volume component 403B, is added to the viscometer flowpath after the reference capillary 404. Additionally, a fluid diverting component 411 is included to select which of the two delay volume components 403A and 403B is before and which is after the reference capillary 404. Transducers may be arranged as known in the art for providing the pressure inputs to the transducer diaphragms, whereby the electrical signals provided by the transducers will be proportional to the differential pressure associated with the flow of fluid through the reference capillary and/or the sample capillary for use in the viscosity analysis. The calculation of relative viscosity may then follow that known for the 2-capillary viscometer.

FIG. 3a represents the embodiment of the subcircuit in configuration A. The fluid viscosity analysis circuit has an inlet tube 401 connected to a source of solvent flow (not shown) commonly used in the art. The inlet tube 401 connects to a capillary tube 402 known as the sample capillary, the other end of the sample capillary 402 is connected to a fluid diverting component 411 (shown as a 4-port, 2-position valve). The fluid passes through the valve 411 by way of a pathway 412, thence onwards to the delay volume component 403A via a tube. The other end of the delay volume component 403A is connected to a reference capillary 404 via a tube, the other end of which is connected to the second delay volume component 403B via a tube. The other end of the second delay volume component 403B is connected back to the fluid diverting component 411 from which fluid in the delay volume component 403B leaves the circuit through the pathway 413 and exits via the tube 405.

FIG. 3b represents the embodiment of the subcircuit in configuration B. The fluid viscosity analysis circuit is substantially identical to that described above for FIG. 3a except that the fluid diverting component 411 has been changed to be configured in its alternative position. Thus, the pathway from the entry point at the entry tube 401 to the exit tube 405 is: sample capillary 402, fluid diverting component 411, fluid pathway 412, delay volume component 403B, reference capillary 404, delay volume component 403A, fluid diverting component 411, fluid pathway 413, and exit tube 405.

An example of a method of operation of the present invention is provided. For the purposes of clarity and to aid in understanding the method, the starting configuration is assumed to be that shown in FIG. 3a. The instrument is in baseline mode when the fluid pathway has only solvent passing through it. Sample solution is injected or enters the circuit by way of the inlet tube 401. When the sample solution passes through the sample capillary 402, there will be a change in fluid pressure sensed by an appropriately placed transducer (not shown). The simultaneous sensing of pressure across the reference capillary 404, sensed by another appropriately placed transducer (See, for example, FIGS. 2a and 2b), will still be that due to the passage of the solvent which is flowing from the delay volume component 403A. Thus the relative viscosity may be computed from the transducer signals as described in, for example, the Haney, Abbott, et al. or de Coral patents. For example, when used in combination with a refractometer or similar concentration detector as the detection device of a gel permeation (or size exclusion) chromatograph, the transducer signals may also be used to determine other information about the sample's properties such as the molecular weight distribution or molecular size distribution.

The method of operation of the subcircuit illustrated in FIG. 3b is identical to the method for FIG. 3a, with the following changes. The fluid diverting component 411 is configured to accept fluid from the sample capillary 402 in the pathway 412 as shown in FIG. 3b. The effect of this configuration of the fluid diverting component 411 is to reverse the position in the fluid pathway of the delay volume components 403A, 403B relative to the reference capillary 404. Thus, the pathway of the fluid from the entry point at the inlet tube 401 becomes: the sample capillary 402, the fluid diverting component 411, the fluid pathway 412, the delay volume component 403B, the reference capillary 404, the delay volume component 403A, the fluid diverting component 411, the fluid pathway 413, and the exit tube 405. Thus the delay volume component 403B is in front of the reference capillary 404 and will provide the local supply of solvent to it. The delay volume component 403A is now downstream of the reference capillary 404. Furthermore, the direction of flow of solvent through the delay volume component 403A is reversed and the sample solution that was passing through it is now flushed out by way of the fluid diverting component 411 via the fluid pathway 413 to the exit pipe 405 where it will take no further part in the analysis process.

Thus, the fluid viscosity analysis circuit may be quickly made ready to accept a further sample for analysis. The fluid pathway may stay in this configuration for the duration of the analysis of the next sample, after which the fluid diverting component 411 may again be activated to align to the alternative configuration. By this time, the delay volume component 403A will be completely replenished with solvent. There is minimal disturbance to the fluid viscosity analysis circuit other than the activation of the fluid diverting component 411 and the consequent reversal of flow direction through a part of the circuit. Depending on the transducer connections, the reversal of flow through the reference capillary 404 may reverse the polarity of the pressure signal, but that effect can be accounted for in processing the transducer signals for a relative viscosity calculation.

Figure 4A:
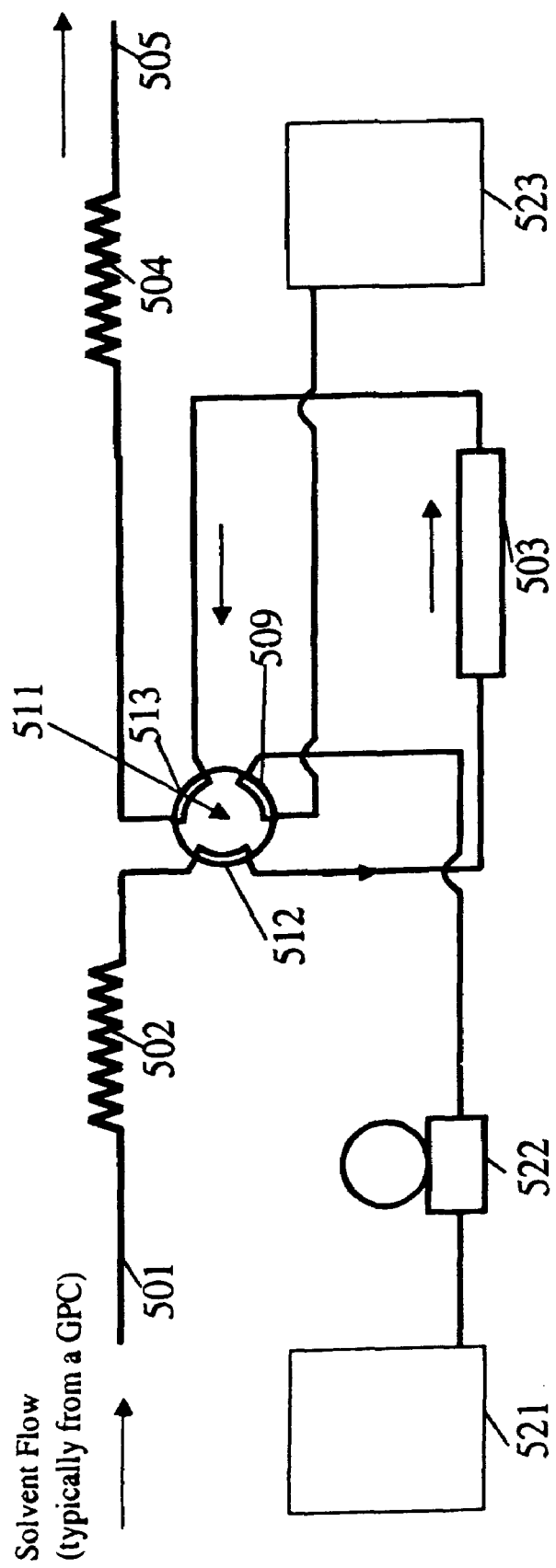
FIG. 4a is a block diagram of one embodiment of the subcircuit of the apparatus with a single delay volume component and a fluid diverting component in orientation A.
Figure 4B:
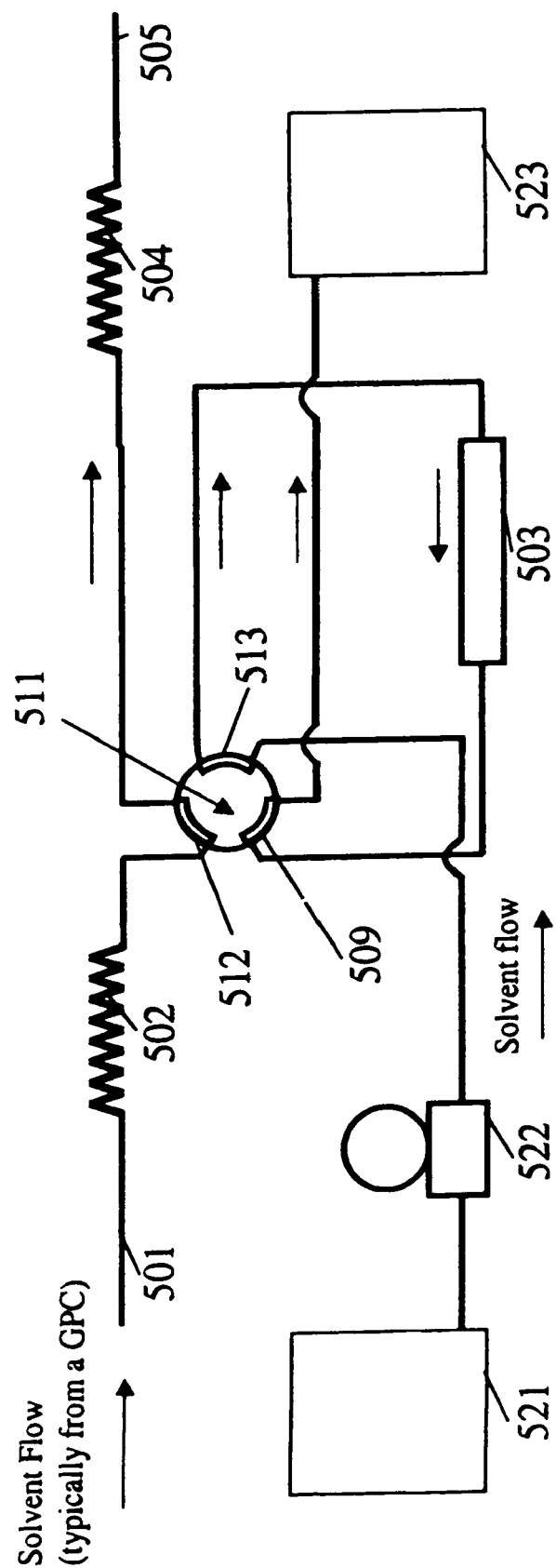
FIG. 4b is a block diagram of one embodiment of the subcircuit of the apparatus with a single delay volume component and a fluid diverting component in orientation B.

FIGS. 4a and 4b represent a further embodiment of the apparatus containing a single delay volume component. A further difference from the embodiments in FIGS. 3a and 3b is that the diverter 511 allows the delay volume component 503 to be connected to either the viscosity measuring circuit or to an external flushing circuit.

FIG. 4a represents another embodiment of the apparatus in a first configuration. The fluid viscosity analysis circuit has an inlet tube 501 connected to a source of solvent flow as commonly used in the industry. The inlet tube 501 connects to a capillary tube 502 known as the sample capillary, the other end of which connects to one port of a fluid diverting component 511 (shown as a 6-port, 2-position valve). The fluid pathway passes through the valve by way of a first channel 512, thence onwards to the delay volume component 503. The other end of the delay volume component 503 is connected back to another port of the fluid diverting component 511 and through a second channel 513 to a capillary tube 504 known as the reference capillary, the other end of which leaves the circuit by way of exit tube 505.

An external fluid circuit consists of a solvent source, the purge solvent reservoir 521, connected to a solvent pump 522, connected to the fluid diverting component 511, connected by way of a third channel 509 to the solvent waste vessel 523. The solvent reservoir 521 and the solvent waste vessel 523 may be the same as those used for the main viscometer circuit or can be separate, conventional units. The solvent pump 522 is typically not activated in this mode other than at start-up to dispel any air bubbles that may be present.

The embodiment of the apparatus as disclosed in FIG. 4a operates in, but is not limited to, substantially the following manner. The sample solution to be analyzed is injected, in the manner commonly known in the art, into the flowing stream of solvent passing through the viscometer circuit by way of the inlet tube 501 through injection.

When the sample solution passes through the sample capillary 502, there will be a change in fluid pressure sensed by an appropriately placed transducer. The simultaneous analysis of pressure across the reference capillary 504 and the sample capillary 502, analyzed by appropriately placed transducers, will still be that due to the passage of solvent which is flowing from the delay volume component 503. The simultaneous sensing of pressure for each capillary allows the determination of relative viscosity as described in, for example, the Haney, Abbott, et al. or de Coral patents. The transducer signals may also be used in combination with the signals produced by a refractometer or similar concentration detector as the detection system of a GPC or SEC to determine other information about the sample's properties such as molecular weight distribution.

FIG. 4b represents yet another embodiment of the apparatus in yet another configuration. After the pressure readings are obtained in the analysis configuration, the fluid diverting component 511 may be switched to realign the valve, in a conventional fashion, such that the delay volume component 503 becomes part of the external circuit, while solvent continues to flow in the main viscosity analysis circuit. In this embodiment, the solvent pump 522 is activated to pump solvent through the external circuit by way of the third channel 513 of the fluid diverting component 511 and into the delay volume component 503 leaving by way of the channel 509 of the fluid diverting component 511 to the waste vessel 523 or alternative exit to waste. This way, the sample solution that was passing through the delay volume component 503 is quickly flushed out to waste before it can pass through the reference capillary 504 to cause a breakthrough peak. When the delay volume component 503 is again full of solvent, the solvent pump is switched off and the fluid diverting component 511 may be switched to realign the valve. In this way, the regenerated delay volume component 503 is restored to the analysis.

Figure 5:
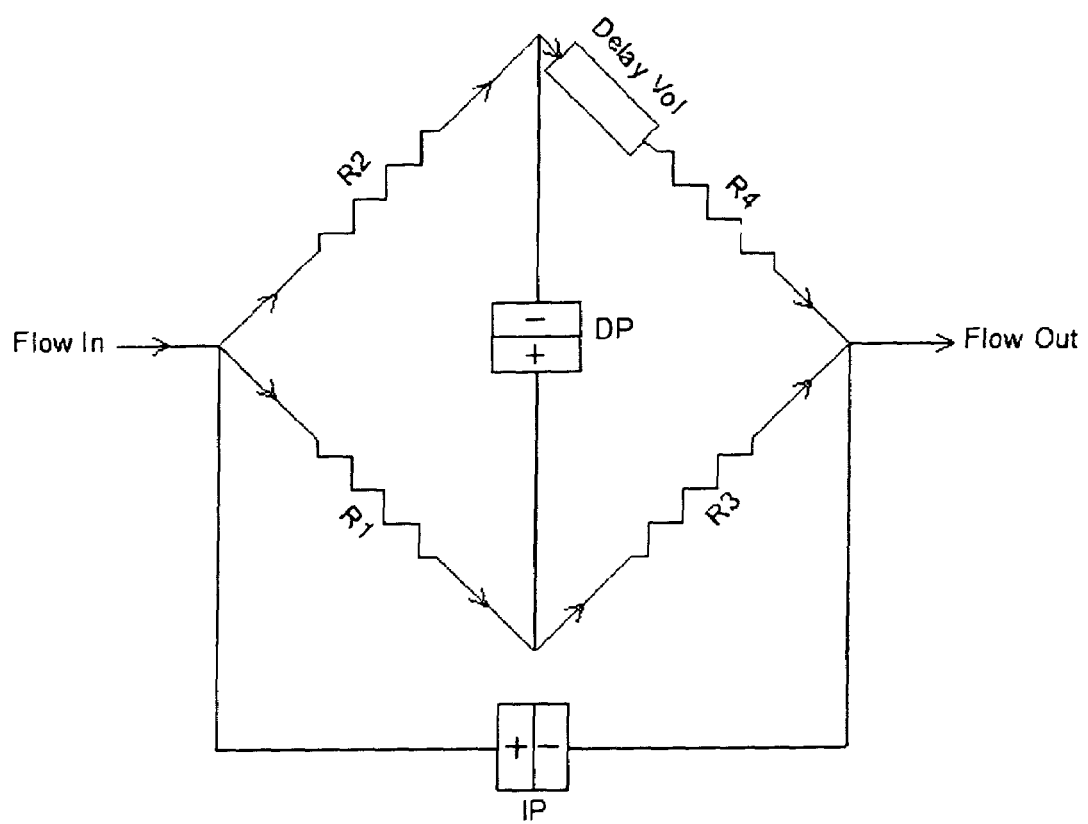
FIG. 5 is a viscometer detector used to illustrate the generation of a breakthrough peak.

FIG. 5 illustrates the most common viscometer detector design. FIG. 5 illustrates a 4-capillary bridge design invented by Dr. Max Haney. The four capillary tubes R1-R4 have internal diameters of approximately 0.25 mm and are arranged in a balanced bridge configuration, analogous to the Wheatstone bridge common in electrical circuits. As above, the differential pressure transducers measure the pressure difference DP across the midpoint of the bridge and the pressure difference IP from inlet to outlet. A delay volume is inserted in the circuit before capillary R4, in order to provide a reference flow of solvent through R4 during elution of, for example, a polymer sample. The requirements of the delay volume are that it must have an internal volume larger than the net elution volume of the GPC column and the flow resistance must be negligible compared to the capillary resistances. The capillary tubes R1-R4 are chosen so that the flow resistances are almost equal. In this case, the DP output signal will be nearly zero and most of the pump pulsations will be cancelled out in the differential bridge measurement.

Figure 6:
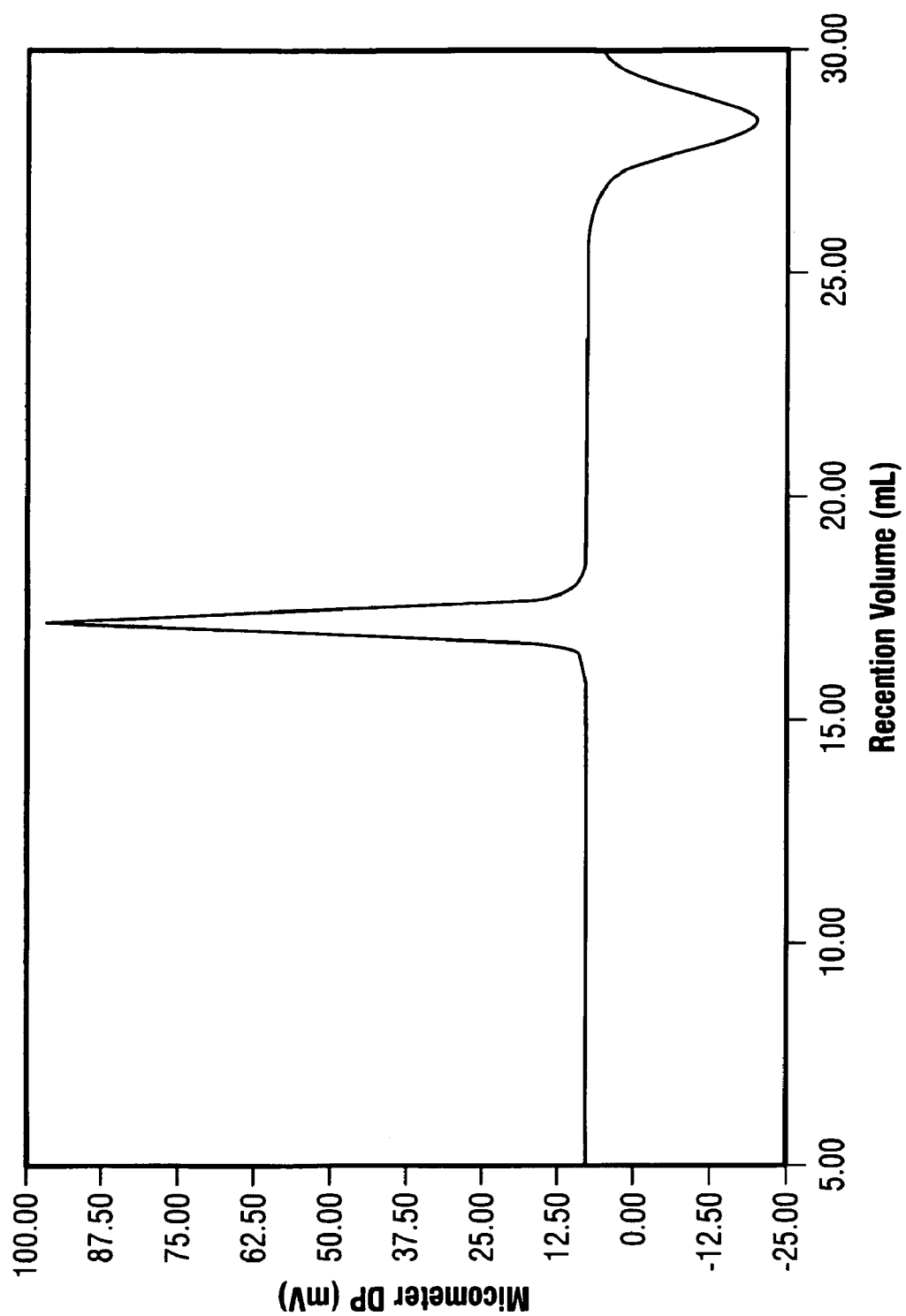
FIG. 6 is a graph of the sample peak and the breakthrough peak by plotting Retention Volume in mL versus Viscometer DP in mV for the output of the viscometer detector illustrated in FIG. 5.

FIG. 6 illustrates the output of the viscometer detector illustrated in FIG. 5, and particularly, the breakthrough peak B. The output of the viscometer detector will respond to the viscosity of the sample as it elutes from a GPC. The first peak A corresponds to the sample as it elutes into capillaries R1, R2 and R3, while solvent flows through capillary R4. The second peak B, the negative peak, illustrates the breakthrough in the delay volume. At this point in time corresponding to the breakthrough peak, the capillary R4 associated with the delay volume contains the sample and other three capillaries R1, R2 and R3 contain solvent. The breakthrough peak is not required for the calculation and is simply an artifact of the measurement. The present invention provides an innovation that eliminates this breakthrough peak in all relevant detectors or sensors.

Figure 7:
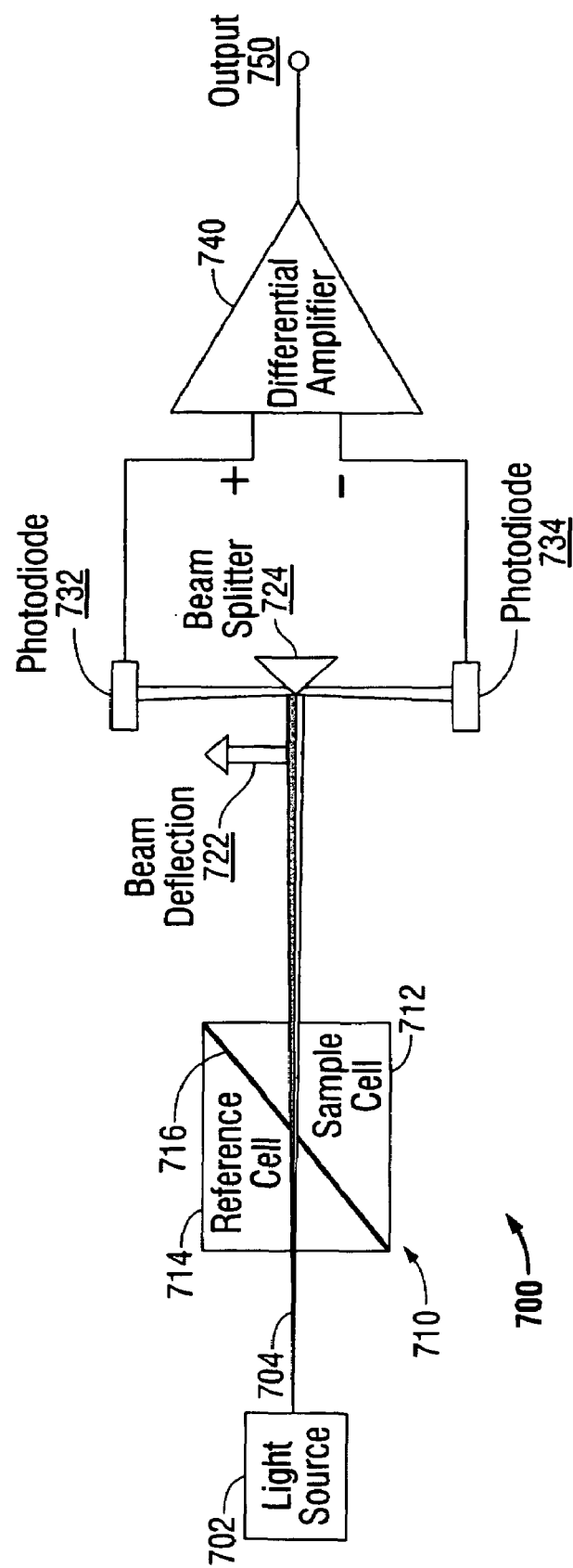
FIG. 7 is a schematic diagram illustrating the principle of differential refractive index (RI) measurement.

FIG. 7 is a schematic diagram illustrating the principle of differential refractive index (RI) measurement by depicting a differential refractive index detector 700. In FIG. 7, a light source 702 provides a light beam 704 to a flow cell 710. The flow cell 710 comprises a sample cell 712 and a reference cell 714. The sample cell 712 and the reference cell 714 are separated by a cell interface 716. The light beam 704 passing through the flow cell 710 may have a beam deflection 722. The light beam 704, deflected or not, passes through the flow cell 710 and engages a beam splitter 724. The beam splitter 724 divides the beam 704 into two beams 704A, 704B. The two beams 704A, 704B engage two photodiodes 732, 734, respectively. The signal from the photodiodes 732, 734 is processed by the differential amplifier 740 and provided to the output 750.

More particularly, the glass flow cell 710 is split into two identical compartments or cells 712, 714. The sample cell 712 contains the sample of interest, which is usually a dilute solution of a polymer solute in a particular solvent. The reference cell 714 contains the particular solvent. The light beam 704 shines through the cell at a 45 degree angle with respect to the interface 716 between the cells 712, 714 and is refracted or deflected at the interface 716 according to Snell's Law of refraction. If both cells 712, 714 contain only solvent then there will be no net refraction, i.e., the beam is not deflected. The beam 704 not being deflected corresponds to the baseline condition in liquid chromatography. But if one cell contains solvent and the other contains a sample, the beam 704 will be deflected in proportion to the difference in refractive index, DRI. In turn, the difference in refractive index, DRI, will be proportional to the concentration of the sample. The range of linear proportion is quite large and the differential refractive index detector 700 works for most samples and solvents. This makes the DRI detector a powerful detector in liquid chromatography, particularly for Gel Permeation Chromatography of polymers, where it is used almost universally.

Figure 8:
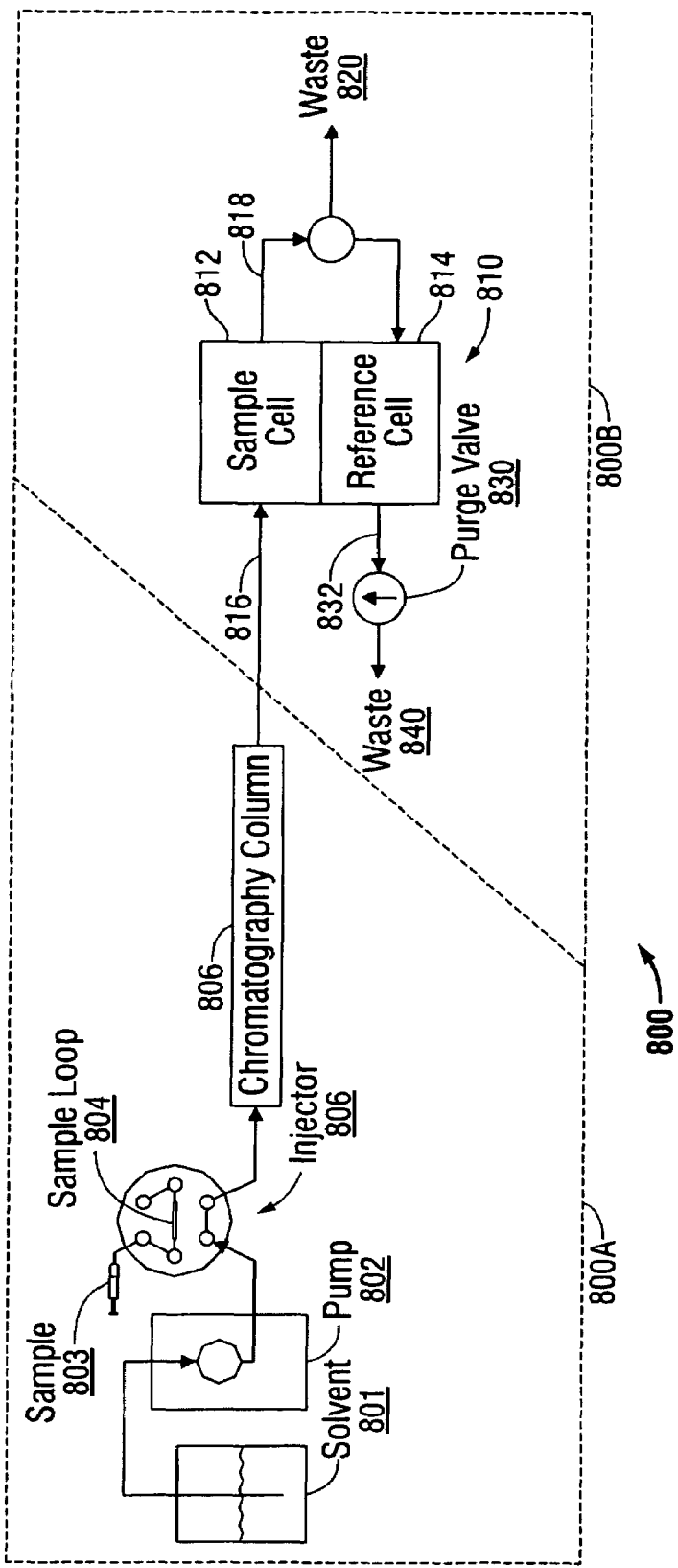
FIG. 8 is a schematic diagram illustrating the flow path for a DRI detector coupled to a GPC.

FIG. 8 is a schematic diagram illustrating a system 800 with a DRI detector 800B coupled to a GPC 800A. Particularly, FIG. 8 shows the flow path for a DRI detector 800B coupled to a GPC 800A. The DRI detector 800B is shown as operated in the conventional manner. The pump 802 provides solvent 801 to the column 806 via the injector 805. The injector 805 operates in association with the sample syringe 803 and the sample loop 804. The sample eluting from the column 806 passes via the line 816 continuously through the sample compartment 812 and to waste 820. However, the reference compartment 814 operates in a "static" mode. The reference cell 814 is initially charged with solvent but then the purge valve 830 is closed and the solvent remains in the reference cell 814 indefinitely. The only problem with the solvent remaining in the reference cell 814 indefinitely is that the refractive index of the static solvent continues to change due to the seals out gassing, etc. The result is drift of the baseline. Eventually, the baseline drift becomes so severe that the operator is forced to purge the reference cell 814 with new solvent and restore the baseline.

Figure 9:
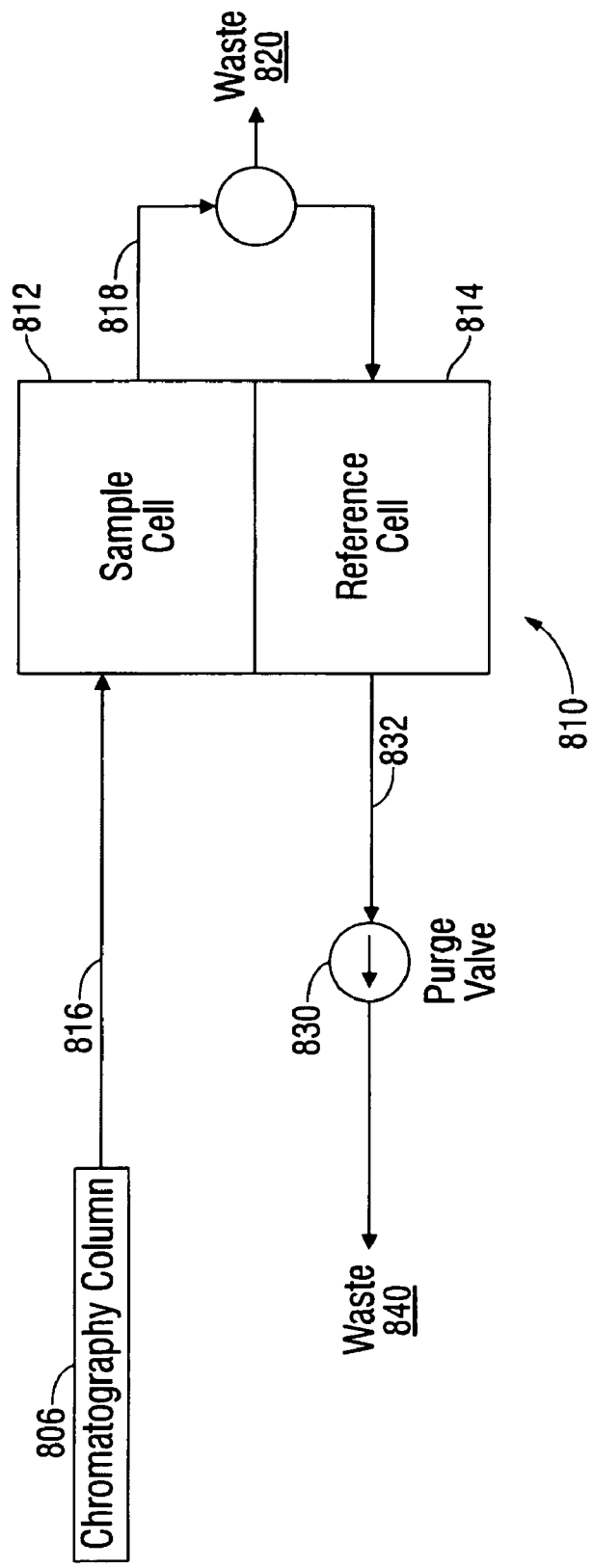
FIG. 9 is a schematic diagram illustrating the conventional manner of purging the solvent into the reference cell.

FIG. 9 is a schematic diagram illustrating the conventional manner of purging the solvent into the reference cell 814. The solvent elutes from the column 806 through the conduit 816 into the sample cell 812. Rather than being dumped to the waste 820, the conduit 818 passes the solvent to the reference cell 814. The solvent passes through the reference cell 814 and exits the conduit 832, passes through the open purge valve 830, and expels to the waste 840. Thus, the solvent is purged through the reference cell 814.

Figure 10:
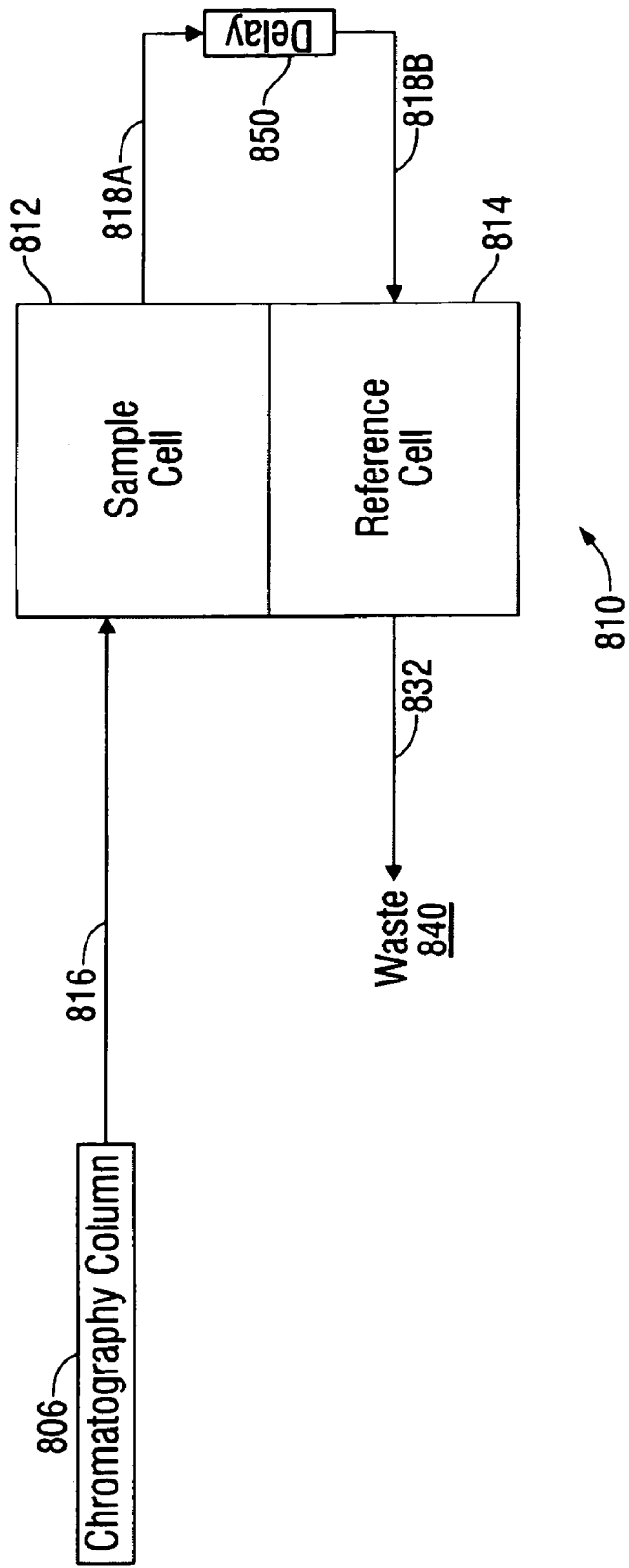
FIG. 10 is a schematic diagram illustrating a delay column used in a manner analogous to the differential viscometer to provide continuous flow of solvent to the reference compartment.

FIG. 10 is a schematic diagram illustrating a delay column 850 used in a manner analogous to the differential viscometer to provide continuous flow of solvent to the reference cell 824. The sample is released from the column 806 and passes to the sample cell 812 via the conduit 816. After passing through the sample cell 812, the sample passes to the delay volume 850 via the conduit 818A, and thereafter to the reference cell 814 via the conduit 818B. Thus, the sample "breaksthrough" to the reference cell 814 thereby interfering with the succeeding sample injection. FIG. 10 illustrates how the delay volume 850 can be used in a manner analogous to the differential viscometer to provide continuous flow of solvent to the reference cell 814. Of course, the same problem observed with the differential viscometer will be observed with the refractive index detector when operated in this manner, i.e., the sample will eventually break through into the reference compartment and yield a "breakthrough peak" that interferes with the succeeding sample injection.

Figure 11:
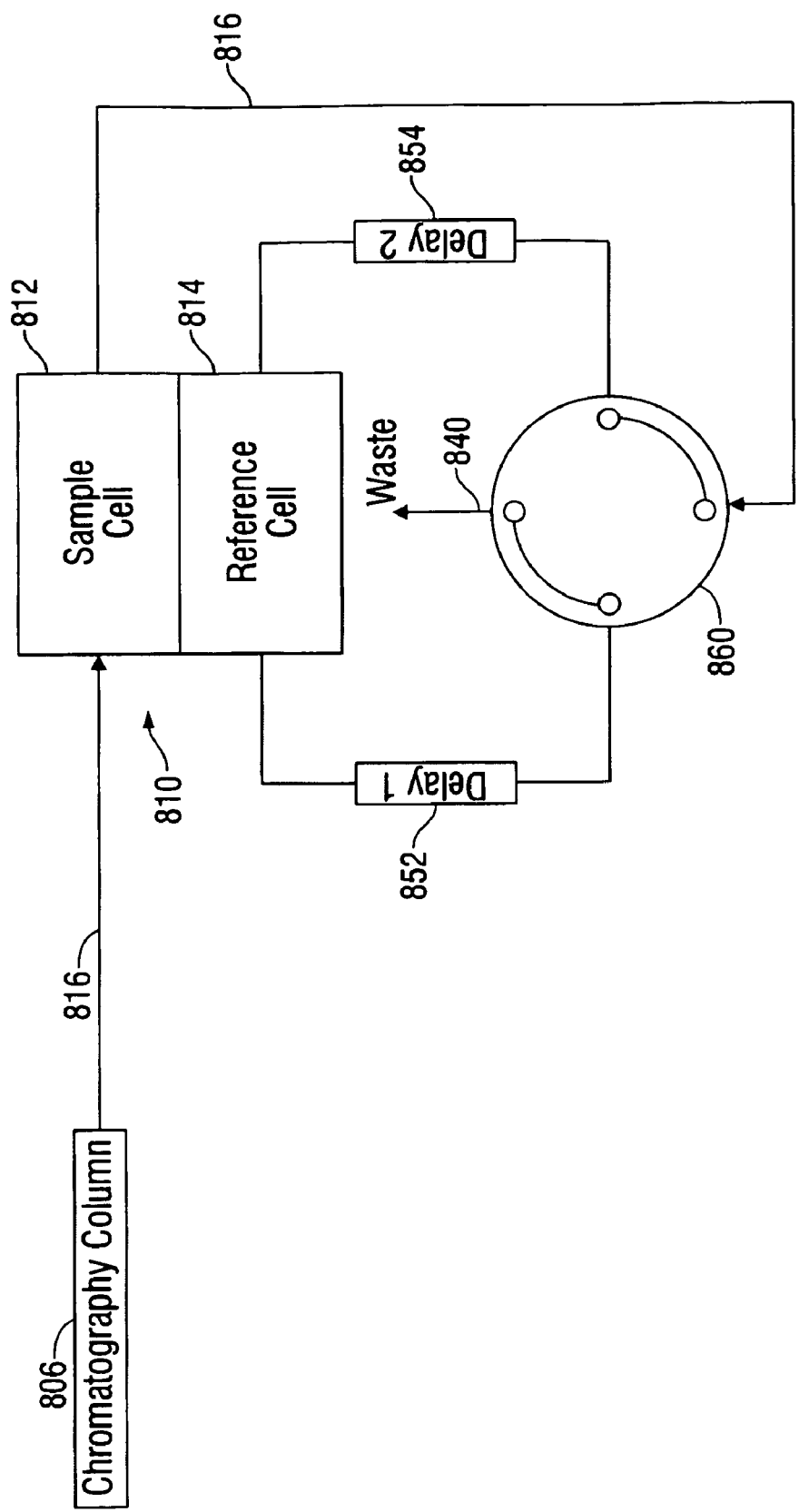
FIG. 11 is a schematic diagram illustrating the no-breakthrough scheme implemented for the viscometer detector will work in an analogous fashion for the RI detector.

FIG. 11 is a schematic diagram illustrating the no-breakthrough differential detector of the present invention. By connecting delay columns 852, 854 at either end of the reference cell 814, in operative association with a switching valve 860 in parallel with the reference cell 814, the breakthrough peak can be eliminated by backflushing the sample. Thus, the implementation of the no-breakthrough differential detector for the viscometer detector will work in an analogous fashion for the refractive index detector, as it will for differential detectors, comparative sensors or any device that involves an analysis between two or more samples or specimen.

FIG. 11 illustrates the sample eluting from the column 806 via the conduit 816. The sample enters the sample cell 812 and exists via the conduit 818 for transfer to the switching valve 860. The switching valve 860 alternately regulates the flow of the sample to waste 840 and the solvent to the reference cell 814.

It may be seen from the preceding description that a new and improved system and method for analysis of fluid properties has been provided. Although very specific examples have been described and disclosed, the embodiments of one form of the apparatus of the instant application is considered to comprise and is intended to comprise any equivalent structure and may be constructed in many different ways to function and operate in the general manner as explained hereinbefore. Accordingly, it is noted that the embodiment of the new and improved system and method described herein in detail for exemplary purposes is of course subject to many different variations in structure, design, application, form, embodiment and methodology. Because many varying and different embodiments may be made within the scope of the inventive concepts herein taught, and because many modifications may be made in the embodiments herein detailed in accordance with the descriptive requirements of the law, it is to be understood that the details herein are to be interpreted as illustrative and not in a limiting sense.

What is claimed is:

1. A method for purging samples from a flow circuit of a detector for analyzing samples comprising the steps of:
   (a) engaging the flow circuit of the detector with a reference fluid,
   (b) accepting a sample in the flow circuit of the detector,
   (c) sensing an attribute of the sample for determining a characteristic of the sample,
   (d) changing the direction of the flow of the sample in the flow circuit, and
   (e) purging the sample from the flow circuit such that the flow circuit is ready to accept another sample.

2. The method for purging samples from a flow circuit of a detector for analyzing samples as defined in claim 1 wherein the step of accepting a sample in the flow circuit of the detector comprises accepting a sample in the flow circuit of a refractive index detector.

3. The method for purging samples from a flow circuit of a detector for analyzing samples as defined in claim 1 wherein the step of accepting a sample in the flow circuit of the detector comprises accepting a sample in the flow circuit of a deflection detector.

4. The method for purging samples from a flow circuit of a detector for analyzing samples as defined in claim 1 wherein the step of accepting a sample in the flow circuit of the detector comprises accepting a sample in the flow circuit of a viscometer.

5. The method for purging samples from a flow circuit of a detector for analyzing samples as defined in claim 1 wherein the step of accepting a sample in the flow circuit of the detector comprises accepting a sample in the flow circuit of a differential detector.

6. The method for purging samples from a flow circuit of a detector for analyzing samples as defined in claim 1 wherein the step of accepting a sample in the flow circuit of the detector comprises accepting a sample in the flow circuit of a detector for analyzing a plurality of samples.

7. The method for purging samples from a flow circuit of a detector for analyzing samples as defined in claim 1 further comprising the step of engaging the detector with a chromatograph.

8. The method for purging samples from a flow circuit of a detector for analyzing samples as defined in claim 7 wherein the step of engaging the detector with a chromatograph comprises the step of engaging the detector with a high-performance liquid chromatograph.

9. The method for purging samples from a flow circuit of a detector for analyzing samples as defined in claim 1 wherein the detector is selected from the group of detectors consisting of flame ionization, thermal conductivity, discharge ionization, electron capture, flame photometric, Hall electrolytic conductivity, helium ionization, nitrogen phosphorus, mass selective, photo-ionization, pulsed discharge ionization and thermal energy analyzer.

10. The method for purging samples from a flow circuit of a detector for analyzing samples as defined in claim 1 wherein the flow circuit comprises a column.

11. The method for purging samples from a flow circuit of a detector for analyzing samples as defined in claim 1 wherein the flow circuit comprises a chromatograph.

12. The method for purging samples from a flow circuit of a detector for analyzing samples as defined in claim 11 wherein the chromatograph is selected from the group consisting of a gel permeation chromatograph (GPC), a reverse phase chromatograph (RPC), gel filtration chromatograph (GFC), a size exclusion chromatograph (SEC), any instrument in which a chemical mixture carried by a liquid or gas is separated into components as a result of differential distribution of solutes, and any combination thereof.

13. A method for purging samples from a flow circuit of a detector for analyzing samples comprising the steps of:
   (a) engaging the flow circuit of the detector with a reference fluid,
   (b) inserting a sample in the flow circuit juxtaposed to the reference fluid,
   (c) sensing an attribute of the sample for determining a characteristic of the sample, and
   (d) deviating the direction of the flow of the sample from the flow circuit for purging the sample from the flow circuit such that the reference fluid is maintained in the flow circuit.

14. The method for purging samples from a flow circuit of a detector for analyzing samples as defined in claim 13 wherein the step of deviating the direction of the flow of the sample from the flow circuit for purging the sample from the flow circuit comprises the steps of changing the direction of the sample in the flow circuit and purging the sample from the flow circuit.

15. The method for purging samples from a flow circuit of a detector for analyzing samples as defined in claim 13 wherein the detector is selected from the group of detectors consisting of flame ionization, thermal conductivity, discharge ionization, electron capture, flame photometric, Hall electrolytic conductivity, helium ionization, nitrogen phosphorus, mass selective, photo-ionization, pulsed discharge ionization and thermal energy analyzer.

16. The method for purging samples from a flow circuit of a detector for analyzing samples as defined in claim 13 wherein the flow circuit comprises a column.

17. The method for purging samples from a flow circuit of a detector for analyzing samples as defined in claim 13 wherein the flow circuit comprises a chromatograph.

18. The method for purging samples from a flow circuit of a detector for analyzing samples as defined in claim 17 wherein the chromatograph is selected from the group consisting of a gel permeation chromatograph (GPC), a reverse phase chromatograph (RPC), gel filtration chromatograph (GFC), a size exclusion chromatograph (SEC), any instrument in which a chemical mixture carried by a liquid or gas is separated into components as a result of differential distribution of solutes, and any combination thereof.

19. An apparatus for purging a sample from a flow circuit of a detector for analyzing the sample comprising:
   (a) the detector comprising a reference cell and a sample cell such that the detector is charged with a reference fluid,
   (b) a switching valve in communication with the sample cell of the detector, and
   (c) one or more delay volumes and the reference cell in communication with the switching valve,
      such that a sample is juxtaposed the reference fluid for engaging the sample cell for analysis, the analyzed sample engages the switching valve for alternately diverting the analyzed sample from the flow circuit and for maintaining the detector charged with the reference fluid.

20. The apparatus for purging a sample from a flow circuit of a detector for analyzing the sample as defined in claim 19 wherein the detector is a refractive index detector.

21. The apparatus for purging a sample from a flow circuit of a detector for analyzing the sample as defined in claim 19 wherein the detector is a deflection detector.

22. The apparatus for purging a sample from a flow circuit of a detector for analyzing the sample as defined in claim 19 wherein the detector is a viscometer.

23. The apparatus for purging a sample from a flow circuit of a detector for analyzing the sample as defined in claim 19 wherein the detector is a differential detector.

24. The apparatus for purging a sample from a flow circuit of a detector for analyzing the sample as defined in claim 19 wherein the detector is a detector for analyzing a plurality of samples.

25. The apparatus for purging a sample from a flow circuit of a detector for analyzing the sample as defined in claim 19 further comprising a chromatograph in operative association with the detector.

26. The apparatus for purging a sample from a flow circuit of a detector for analyzing the sample as defined in claim 25 wherein the chromatograph comprises a high-performance liquid chromatograph.

27. The apparatus for purging a sample from a flow circuit of a detector for analyzing the sample as defined in claim 19 wherein the flow circuit comprises a chromatograph.

28. The method for purging samples from a flow circuit of a detector for analyzing samples as defined in claim 27 wherein the chromatograph is selected from the group consisting of a gel permeation chromatograph (GPC), a reverse phase chromatograph (RPC), gel filtration chromatograph (GFC), a size exclusion chromatograph (SEC), any instrument in which a chemical mixture carried by a liquid or gas is separated into components as a result of differential distribution of solutes, and any combination thereof.

29. A system for analyzing a sample comprising:
(a) a flow circuit,
(b) a column operatively associated with the flow circuit, and
(c) a detector operatively associated with the flow circuit and the column for detecting the sample, such that a reference fluid is engaged in the flow circuit, the sample is accepted in the flow circuit, the detector determines a characteristic of the sample, the direction of the flow of the sample in the flow circuit is changed, and the sample is purged from the flow circuit such that the flow circuit is ready to accept another sample.

30. The system for analyzing a sample as defined in claim 29 further comprising a chromatograph selected from the group consisting of a gel permeation chromatograph (GPC), a reverse phase chromatograph (RPC), gel filtration chromatograph (GFC), a size exclusion chromatograph (SEC), any instrument in which a chemical mixture carried by a liquid or gas is separated into components as a result of differential distribution of solutes, and any combination thereof.

31. A system for analyzing a sample comprising:
(a) a chromatograph selected from the group consisting of a gel permeation chromatograph (GPC), a reverse phase chromatograph (RPC), gel filtration chromatograph (GFC), a size exclusion chromatograph (SEC), any instrument in which a chemical mixture carried by a liquid or gas is separated into components as a result of differential distribution of solutes, and any combination thereof,
(b) a detector comprising a reference cell and a sample cell such that the detector is charged with a reference fluid,
(b) a switching valve in communication with the sample cell of the detector, and
(c) one or more delay volumes such that the reference cell is in communication with the switching valve,
such that a sample is juxtaposed the reference fluid for engaging the sample cell for analysis, the analyzed sample engages the switching valve for alternately diverting the analyzed sample from the flow circuit and for maintaining the detector charged with the reference fluid such that the detector is ready to accept another sample.

* * * * *